United States Patent [19]
Nagamori et al.

[11] Patent Number: 5,804,441
[45] Date of Patent: Sep. 8, 1998

[54] HUMAN HEPATOMA-DERIVED CELL LINE FLC-4 AND METHOD FOR PRODUCING USEFUL POLYMERS BY CULTURING THE CELL LINE

[75] Inventors: Seishi Nagamori; Satoshi Hasumura; Masaaki Kawada; Tomokazu Matsuura, all of Tokyo; Satoru Mizutani; Hitoshi Yoshida, both of Kanagawa, all of Japan

[73] Assignee: Kirin Beer Kabushiki Kaisha, Tokyo, Japan

[21] Appl. No.: 554,914

[22] Filed: Nov. 9, 1995

[51] Int. Cl.[6] ............................. C12N 5/08; C12P 21/04
[52] U.S. Cl. .................... 435/370; 435/366; 435/70.3; 435/70.1
[58] Field of Search .................... 435/366, 370, 435/70.1, 70.3

[56] References Cited

PUBLICATIONS

S. Nagamori et al., "Information on Cell Lines", Human Cell, vol. 1, No. 1, Mar. (1988), (English translation).
S. Hasamura et al., Establishment and Characterization of a Human Hepatocellular Carcinoma Cell Line JHH–4, Human Cell, vol. 1, No. 1, (1988), pp. 98–100.

S. Nagamori., "Protein Secretion of Human Cultured Liver Cells", Human Cell, vol. 1, No. 4, (1988), pp. 382–390.
S. Homma et al., "Establishment and Characterization of a Human Hepatocellular Carcinoma Cell Line JHH–7 Producing α–Fetoprotein and Carcinoembryonic Antigen", Human Cell, vol. 3, No. 2, (1990), pp. 152–157.
M. Kawada et al., "New Liver Support System Composed of Functional Human Cells and a Radial–Flow Bioreactor", Human Cell, vol. 7, No. 2, (1990), pp. 95–100.
Matsuura et al, *Acta. Med. Okayama,* vol. 37, pp. 341–352 (1983).
Li et al, *J. China Med Univ.,* 17(4) 1988, pp. 259–263.
Saint Ruf, et al, *Oncogene,* 7(8) 1992, pp. 1557–1565.
Wuu et al, Cancer Genet. Cytogenet., 26:279–286 (1987).

*Primary Examiner*—Irene Marx
*Attorney, Agent, or Firm*—Foley & Lardner

[57] ABSTRACT

Human hepatoma-derived cell line FLC-4 (deposited with the National Institute of Bioscience and Human-Technology, the Agency of Industrial Science and Technology under Accession Number FERM BP-5165), as well as a method for large-scale production of albumin by culturing the cell line with a radial-flow type bioreactor are provided.

5 Claims, 9 Drawing Sheets

HUMAN HEPATOMA-DERIVED CELL LINE FLC-4 AND METHOD FOR PRODUCING USEFUL POLYMERS BY CULTURING THE CELL LINE

BACKGROUND OF THE INVENTION

1. Technical Field

The present invention relates to novel human hepatoma-derived cell line FLC-4 and a method for producing a useful polymer by culturing the cell line.

2. Description of the Related Art

The liver performs various functions including the synthesis and secretion of most serum proteins such as albumin and lipoproteins, the synthesis of export lipids coupling to proteins, detoxication, the formation and secretion of bile, blood sugar regulation by the production of sugar, urea synthesis caused by the resulting amino acid degradation, the activation of vitamins, the synthesis and degradation of glycogen, the synthesis of glutathione and metallothionein, and the like.

Hence, many researchers have cultured liver cells in order to study their functions which are more abundant than found in other tissue cells, such as their most characteristic ability to synthesize and secrete plasma proteins, and these functions have been utilized for many years.

With the recent progress of biotechnology, useful substances are actively produced by genetic recombination and cell fusion methods. As a result, animal cell cultivation has become more important than ever. Since the aforementioned abilities of liver cells to synthesize albumin, lipoproteins, export lipids, urea, glycogen, glutathione, metallothionein and the like are more abundant than those of other tissue cells, they are interesting hosts for the production of substance by animal cell cultivation. In particular, hepatoma cells have high proliferation potency and are therefore promising hosts for the production of substance.

However, cultivation techniques are not satisfactory at present for maintaining hepatocytes (normal liver cells) capable of producing plasma proteins during cultivation periods. For the purpose of obtaining substitutes for hepatocytes, studies have been conducted actively for creating hepatoma cell-derived cell lines that have characters peculiar to hepatocytes (normal liver cells) and which are capable of producing liver-specific proteins such as albumin.

Known human-derived hepatoma cell lines include: HLF (Okayama University, medical school: 1975), HLE, c-1 (Okayama University, medical school: 1975), HuH-6 clone 5 (Okayama University, medical school: 1976), HuH-7 (Okayama University, medical school: 1979), C-HC-4 (Hokkaido University, school of medicine: 1979), HCC-M (Keio University, school of medicine: 1980), JHH-1 (The Tokyo Jikei University School of Medicine: 1980), JHH-2 (The Tokyo Jikei University School of Medicine: 1982), JHH-4 (The Tokyo Jikei University School of Medicine: 1983), KIM-1 (Kurume University, school of medicine: 1983), JHH-5 (The Tokyo Jikei University School of Medicine: 1984), JHH-6 (The Tokyo Jikei University School of Medicine: 1984), OHR (Showa University, school of medicine: 1985), KMCH-1 (Kurume University, school of medicine: 1985), KMG-A (Kurume University, school of medicine: 1985), JHH-7 (The Tokyo Jikei University School of Medicine: 1986), JHC-1 (The Tokyo Jikei University School of Medicine: 1986), KYN-1 (Kurume University, school of medicine: 1986), KYN-2 (Kurume University, school of medicine: 1987), HCC-T (Keio University, school of medicine: 1986), HPT-NT/D3 (Kyushu University, faculty of medicine: 1986), Hep-tabata (Mie University, Faculty of Medicine: 1986), HuCC-T1 (Toyama Medicine and Pharmaceutical University, faculty of medicine: 1987), HuH-28 (Okayama University, medical school: 1987). See HUMAN CELL, Vol. 1, No.1, p.106–126, 1988.

Moreover, attempts have been made aggressively to prepare artificial livers by culturing liver cells using bioreactors (JP 6509476 W). For encouraging the practical use of artificial livers, it is necessary to develop a light and small-sized bioreactor apparatus and its peripheral devices. To this end, the creation of cell lines capable of producing the necessary and sufficient amounts of liver-specific proteins in small amounts of media is also desired.

DISCLOSURE OF THE INVENTION

SUMMARY OF THE INVENTION

Accordingly, an object of the present invention is to provide novel human hepatoma-derived cell line FLC-4 capable of producing a liver-specific protein in high yield and a method for producing a useful polymer by culturing the cell line.

For attaining the aforementioned object, the inventors studied various serum-free cultured mutants that were derived from known human hepatoma-derived strain JHH-4 (HUMAN CELL, Vol. 1, No. 1, p.98–100, 1988). As a result, they found a novel human hepatoma-derived cell line named FLC-4 using the production of a liver-specific protein albumin as an indicator. The present invention has been accomplished on the basis of this finding.

The present invention provides novel human hepatoma-derived cell line FLC-4 capable of producing a liver-specific protein albumin in high yield.

The present invention also provides a method for producing a useful liver-specific proteinaceous substance in high yield, by culturing novel human hepatoma-derived cell line FLC-4.

Moreover, the present invention provides a method for producing a liver-specific protein albumin by culturing novel human hepatoma-derived cell line FLC-4.

DETAILED DESCRIPTION OF THE INVENTION

The present invention relates to novel human hepatoma-derived cell line FLC-4 and a method for producing a useful polymer by culturing the cell line.

THE ESTABLISHMENT AND CHARACTERIZATION OF HUMAN HEPATOMA-DERIVED CELL LINE FLC-4

Figure 1:
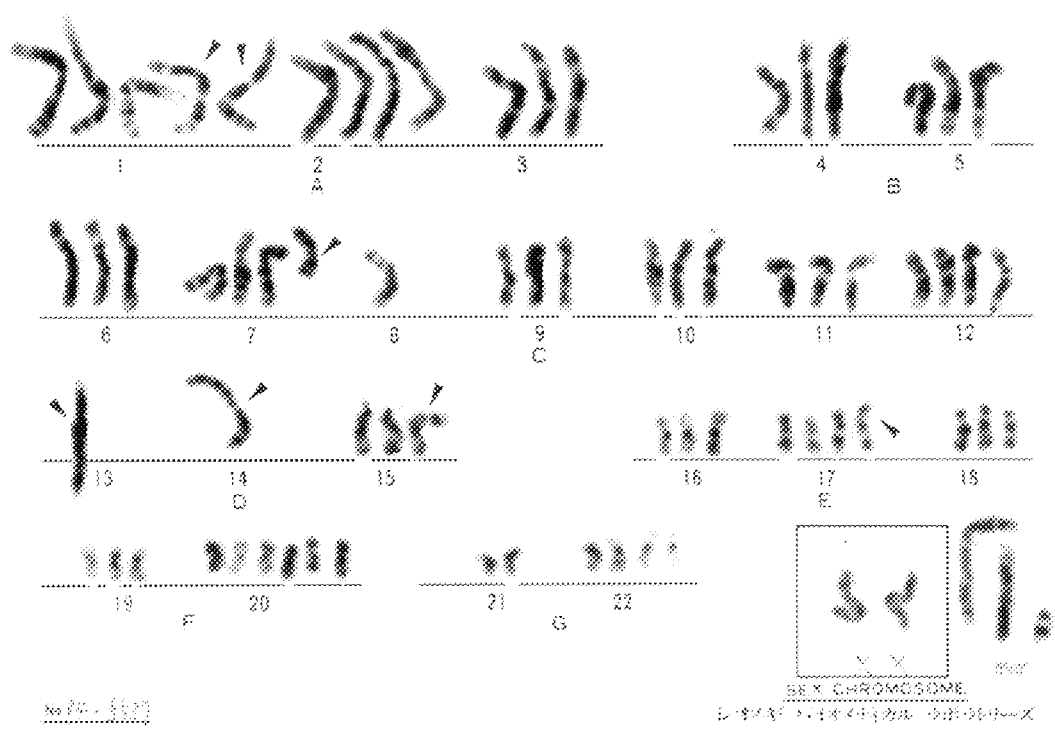
FIG. 1 shows the karyotype of chromosomes in strain JHH-4.

The novel human hepatoma-derived cell line FLC-4 of the present invention has been obtained by serum-free culture mutation of known human hepatoma-derived strain JHH-4. The novel cell line FLC-4 of the present invention is similar to the parent strain JHH-4 in morphology and biological properties (details are given in HUMAN CELL 1 (1): p.98–100, 1988) but different in karyotype as follows:

Strain JHH-4 has 74 chromosomes (pseudotriploid) with the following karyotype: 74, +1, der(1)t(1;14) (p11;q11)×2, +2×2, +3, +4, +5, +6, +7, +add(7) (q11.2), −8, +9, +10, +11, +12×2, −13, add(13) (q34), −14, add(14) (p11), + der(15)t (15;21) (p11;q11), +16, +17, +i(17) (q10), +18, +19, +20×4, +22×2, +3mar. FIG. 1 shows the karyotype of strain JHH-4

Figure 2:
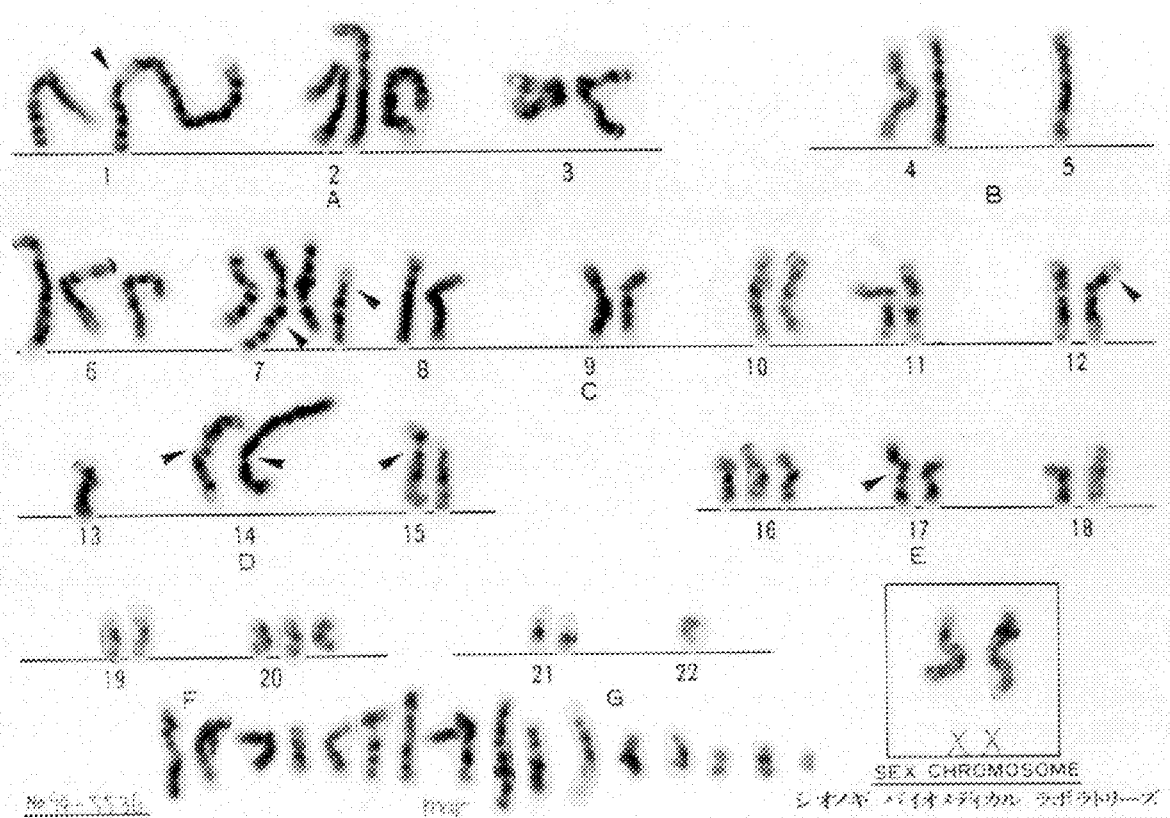
FIG. 2 shows the karyotype of chromosomes in cell line FLC-4.

Cell line FLC-4 has 65 chromosomes with the following karyotype: 65, XX, add(1) (p11), +2, −5, +6, +add(7) (p11), +add(7) (q32), add(12) (p13), −13, add(14) (p11), add(14) (p11), +der(15)t(15;21) (p11;q11), +16, +i(17) (q10), +20, −22, +16mar. FIG. 2 shows the karyotype of cell line FLC-4.

The novel human hepatoma-derived cell line FLC-4 has been deposited with the National Institute of Bioscience and Human-Technology, the agency of Industrial Science and Technology, 1-3, Higashi 1 chome, Tsukuba-shi, Ibaraki-ken 305, Japan, Ibaraki-ken 305, Japan, under Accession Number FERM BP-5165 (deposition date: Jul. 14, 1995).

A method for producing a useful liver-specific proteinaceous substance, more specifically, albumin in high yield by culturing the novel human hepatoma-derived cell line FLC-4 will now be explained in greater detail with reference to the following example which is by no means intended to limit the scope of the present invention.

EXAMPLE

The production of a liver-specific protein albumin by culturing the novel human hepatoma-derived cell line FLC-4 is illustrated. In a comparative example, the same procedure was performed with strain JHH-7 rather than cell line FLC-4.

The radial-flow type bioreactor (RA-400, Biott, Tokyo, Japan) used in cultivation was developed for high-density and large-scale cultivation of adhesion-dependent animal cells. The body of this reactor is a cylinder of 5 cm in diameter and 20 cm in height and the capacity for carrier is 400 ml.

Siran (Schott, Glaswerke Co., Ltd, Germany) was used as a carrier. Siran is a spherical porous glass bead of about 0.6 cm in diameter with a void of 50% and a surface area of 900 $cm^2$/ml-matrix, which has a honeycombed inner structure. Cultured cells attach to the outer and inner surface of the siran carrier. The number of adhering cells in the 400 ml reactor was calculated to be at least $1\times10^{10}$.

The medium was based on ASF104 for serum-free cultivation (Ajinomoto CO., LTD., Tokyo, Japan) to which 2% FBS was added for improving the adhesion of cultured cells to the carrier. In addition, dipeptides (500 mg/l) prepared by coupling thermal degradation-susceptible glutamine with glycine or alanine were added to the medium for enabling autoclaving. The didpeptides were replaced with monomeric glutamine (1000 mg/l) after 11 days of the cultivation.

The medium supply rate was set in the range of 10–20 l/day, the medium circulation speed was set in the range of 100–400 l/day, and the oxygen supply rate was set in the range of 50–400 ml/min.

More specifically, the cells were cultured as follows:

Each of FLC-4 and JHH-7 cells was subcultured in a flask with an adhesion area of 175 $cm^2$ (FALCON 3028, BECTON DICKINSON CO., U.S.A) up to 96 flasks and the subcultured cells were scratched off using 2% EDTA-supplemented trypsin (25 usp unit/ml). The cells were suspended in a medium of about 20 ml and inoculated in a solution at a concentration of $1.6\times10^8$ cells/solution. The inoculation solution was charged in the reactor. The amount of the culture solution in the reactor was 100–150 ml.

After the beginning of the cultivation, cell proliferation caused an increase in the carbon dioxide concentration and lactic acid production, which led to a lower pH. The adhesion and proliferation of the cells in the reactor were confirmed by measuring the oxygen and glucose consumption rates.

1) Measurement of albumin

Figure 3:
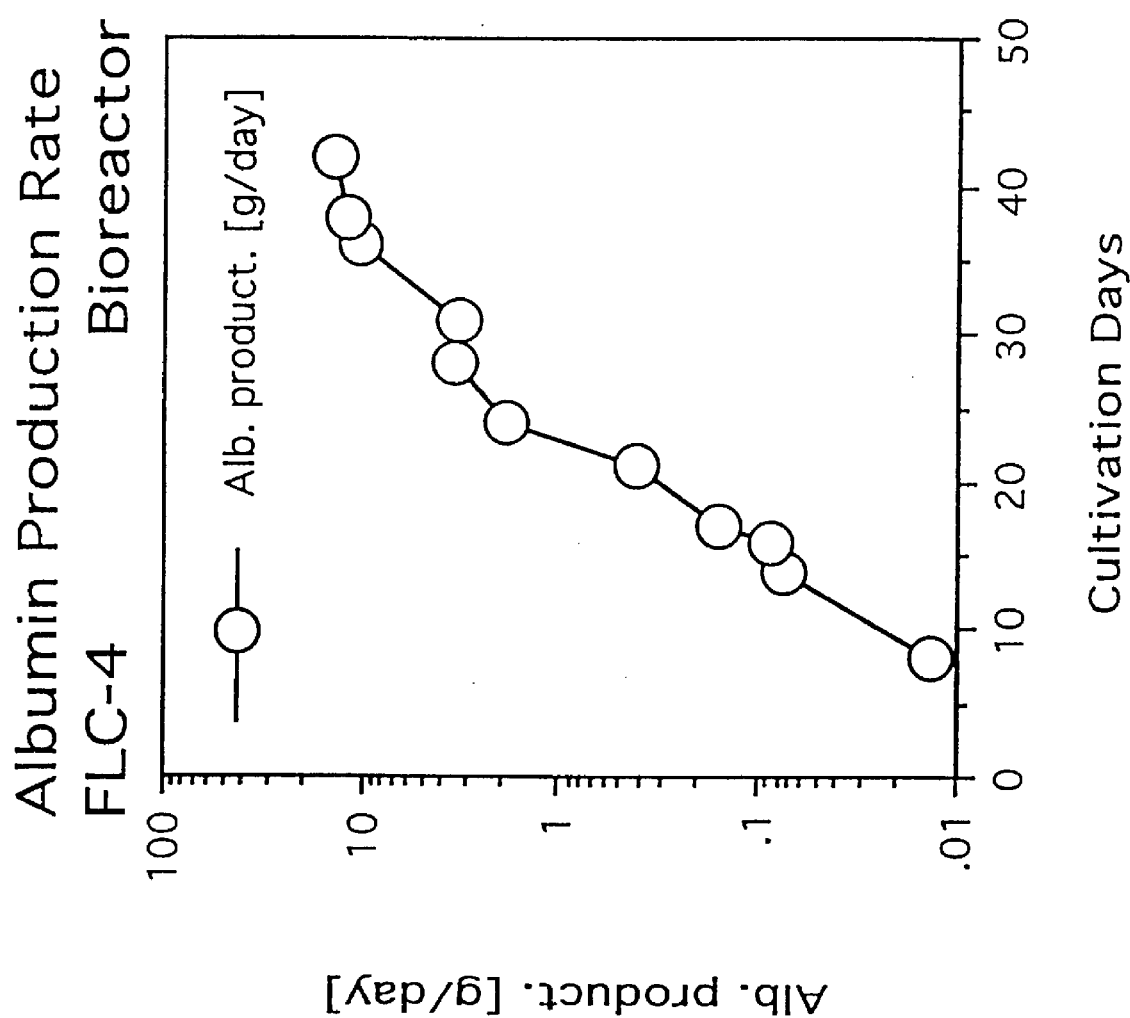
FIG. 3 shows the daily albumin production rate of cell line FLC-4.
Figure 4:
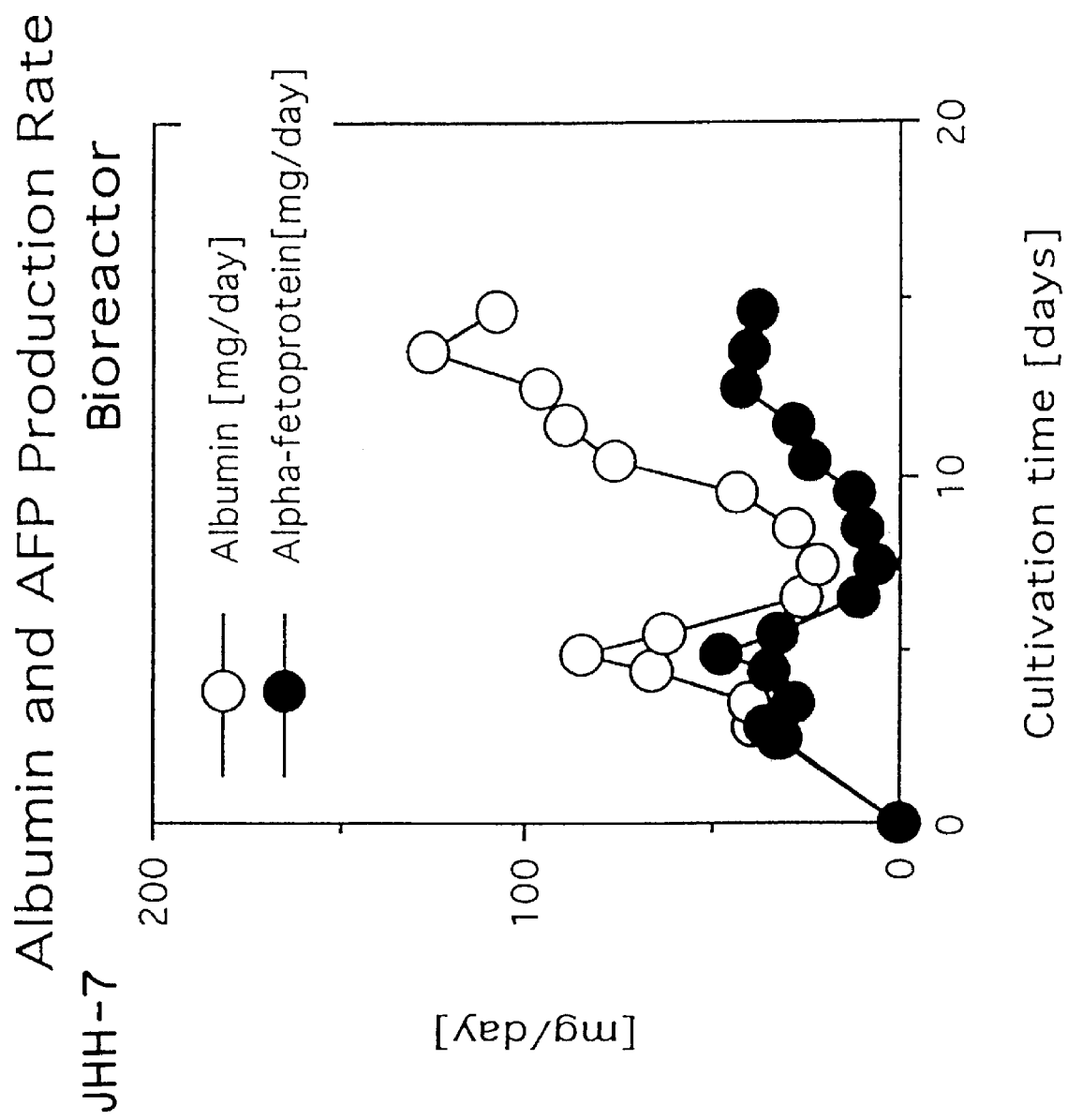
FIG. 4 shows the daily albumin and AFP (alpha fetoprotein) production rate of strain JHH-7.

Albumin was measured by an enzyme-linked immunosorbent assay (ELISA) method and the rate of its daily production was calculated. Cell line FLC-4 produced albumin in a maximum of 13–14 g per day. Results are shown in FIG. 3. In the comparative example, strain JHH-7 produced albumin in a maximum of 127.2 mg per day. The curves of the albumin and AFP production rates of strain JHH-7 had 2 peaks which were correlated with glucose and oxygen consumption rates. Results are shown in FIG. 4.

2) Measurement of glucose and oxygen consumption rates

Figure 5:
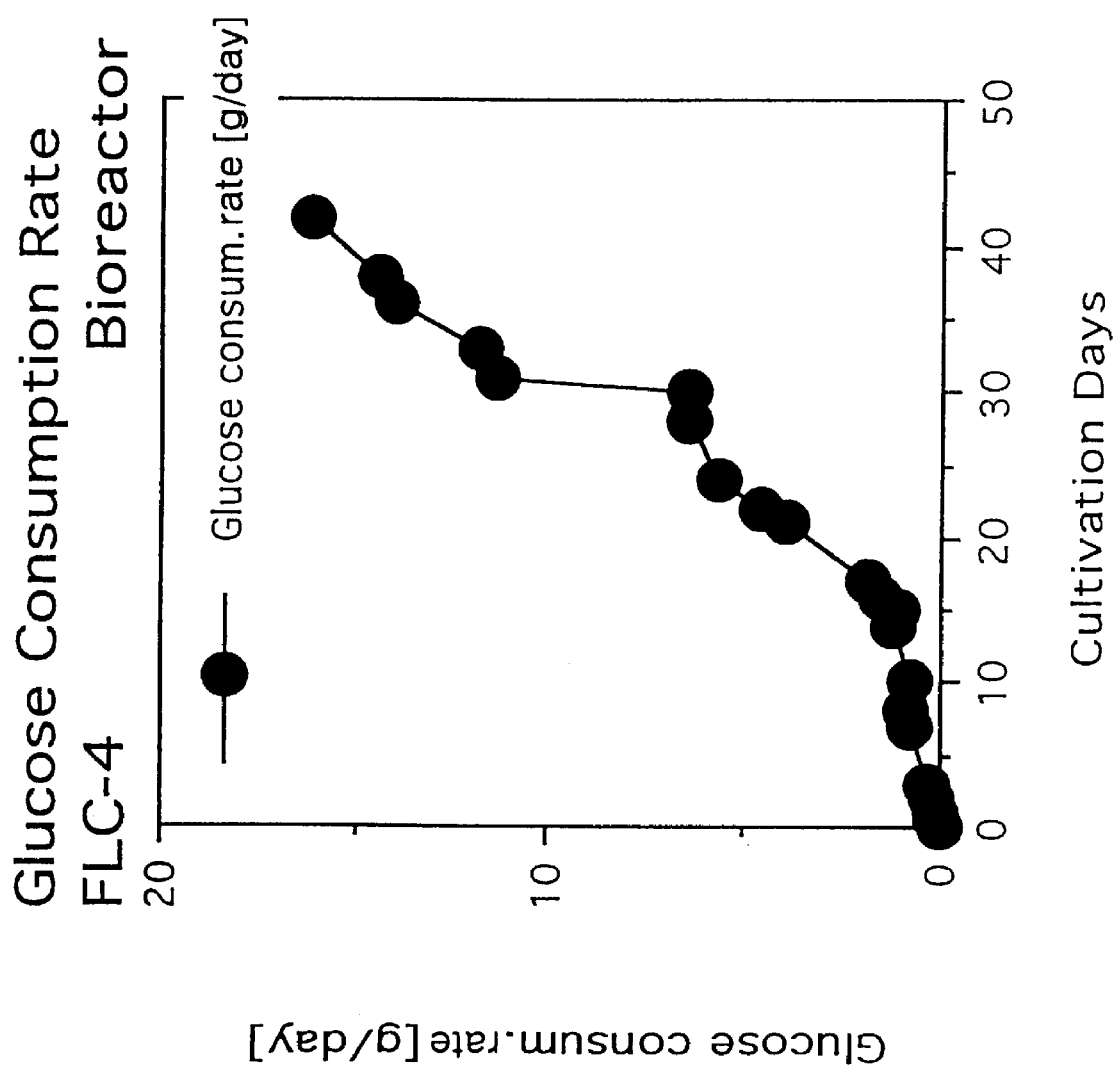
FIG. 5 shows the daily glucose consumption rate of cell line FLC-4.
Figure 6:
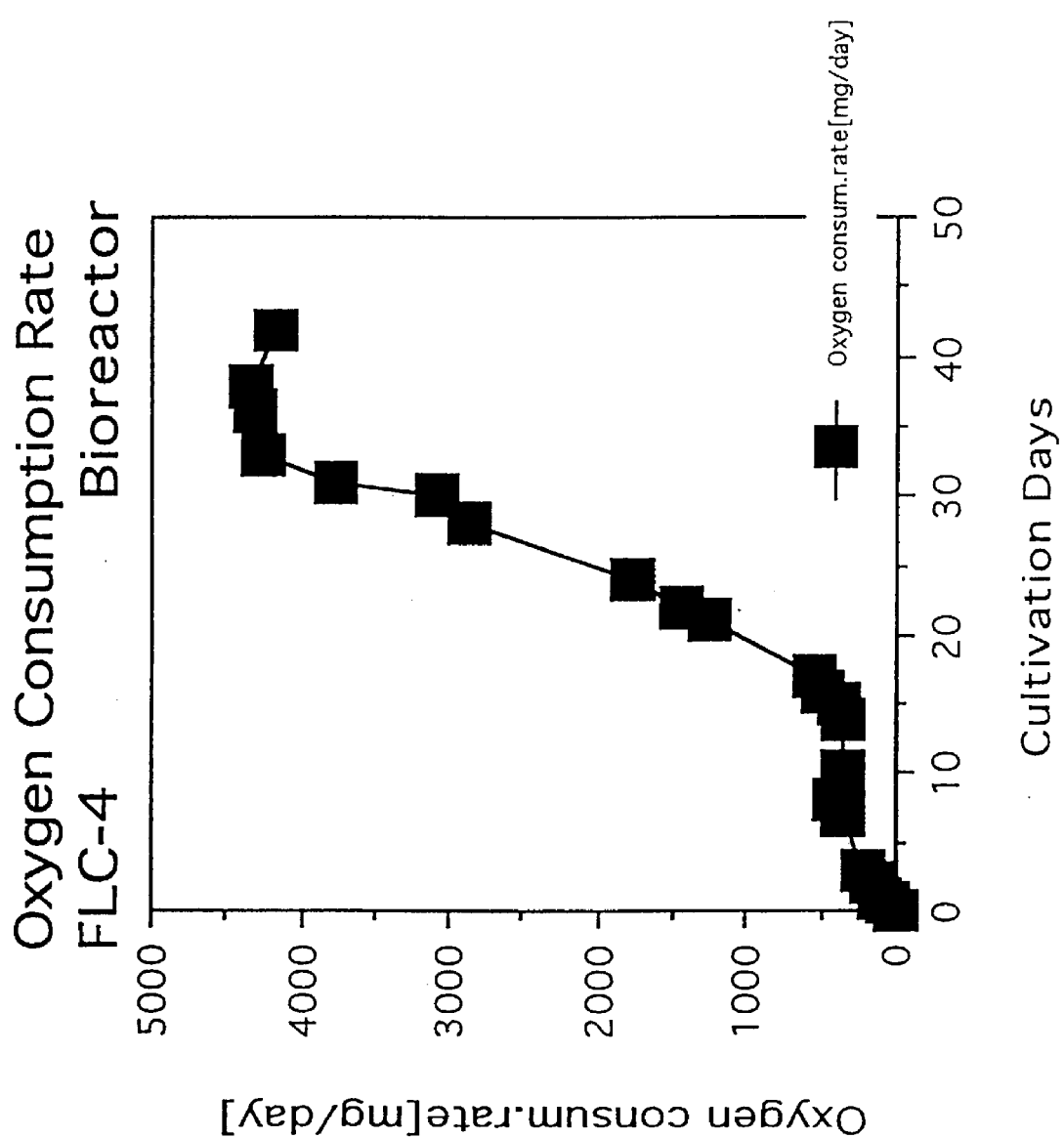
FIG. 6 shows the daily oxygen consumption rate of cell line FLC-4.
Figure 7:
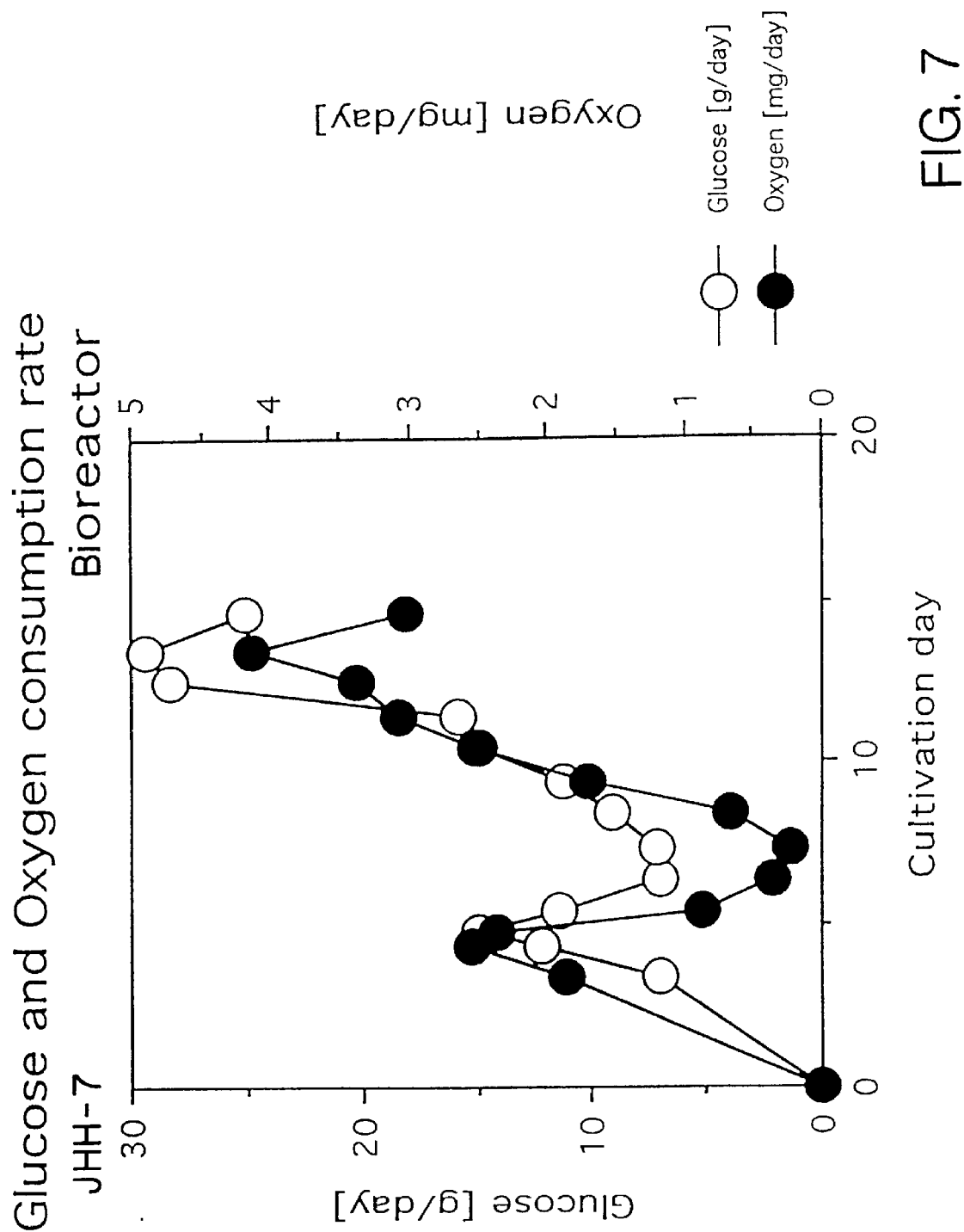
FIG. 7 shows the daily glucose and oxygen consumption rate of strain JHH-7.

The glucose concentration of the collected culture solution was determined by adding 20 µl of the sample to 3 ml of the solution contained in a glucose measurement kit (Glucose C Test Wako, Wako Pure Chemical Industries Ltd.) and measuring the absorbance at 505 nm with a spectrophotometer (UV-160A, Shimadzu Corp.). The daily glucose consumption rate of cell line FLC-4 was calculated from the data obtained for glucose concentration and the preset medium supply speed. Results are shown in FIG. 5. The oxygen consumption rate was determined from the record on the reactor. Results are shown in FIG. 6. The glucose and oxygen consumption rates of strain JHH-7 were measured by the same method in the comparative example and results are shown in FIG. 7.

3) Measurement of ammonia and urea

Figure 8:
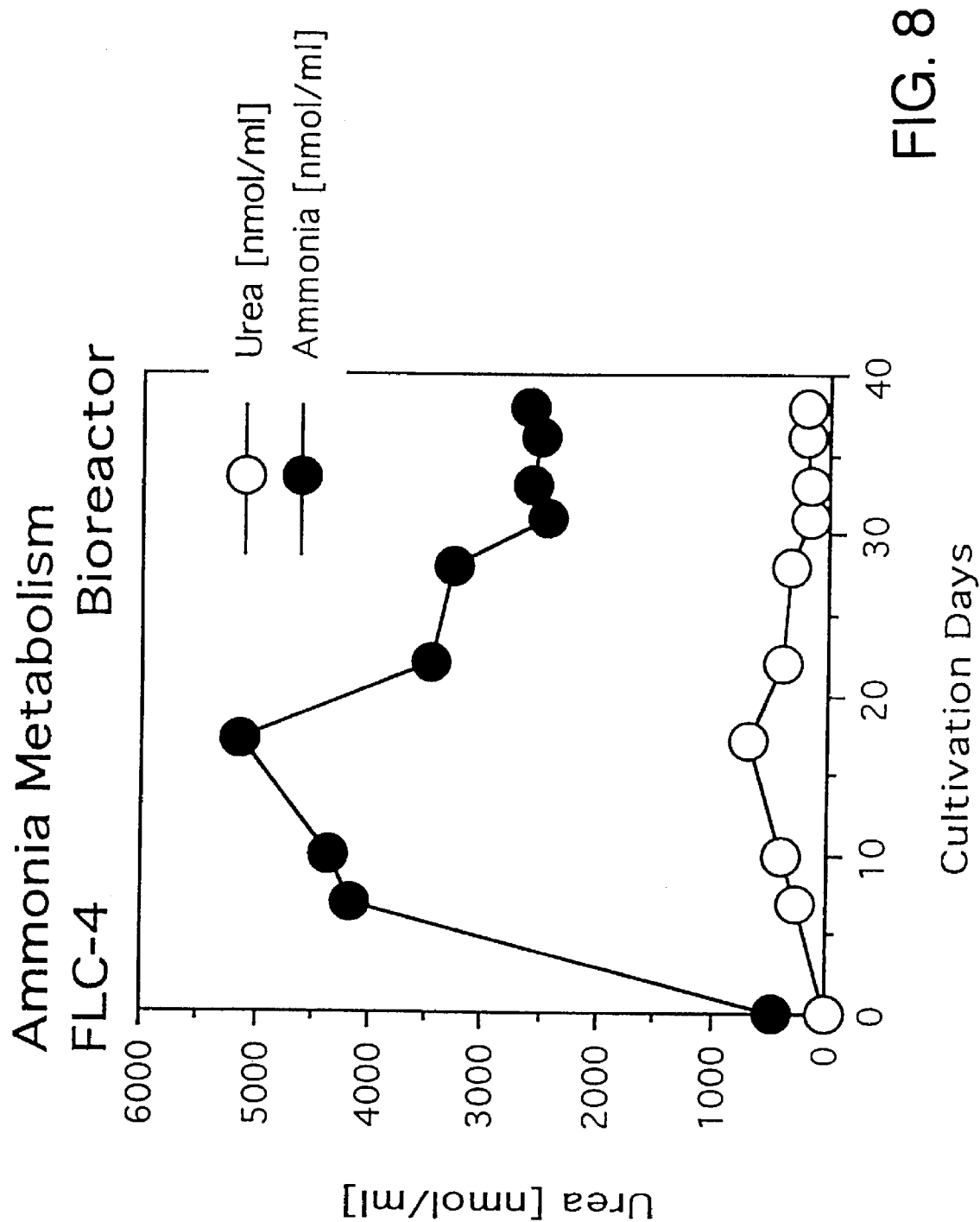
FIG. 8 shows the daily ammonia and urea metabolism of cell line FLC-4.
Figure 9:
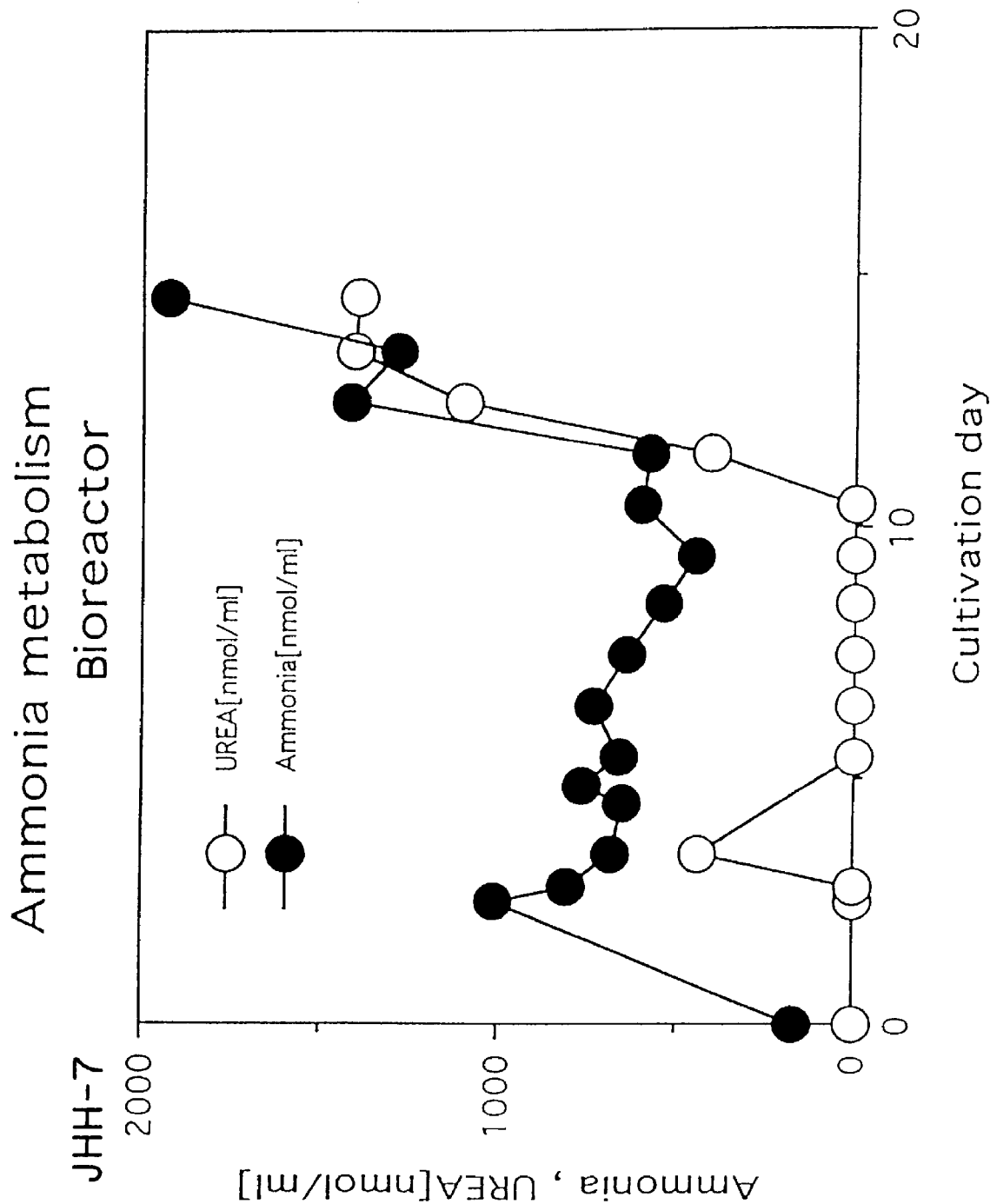
FIG. 9 shows the daily ammonia and urea metabolism of strain JHH-7.

Ammonia and urea were determined with an auto high-performance amino acid analyzer (JLC-300, auto high-performance liquid chromatography, JEOL Ltd.) and the daily production (metabolism) rates of ammonia and urea of cell line FLC-4 were calculated. The production rates of ammonia and urea were stably low in a prolonged cultivation (40 days), demonstrating that no excess amount of ammonia was accumulated. Results are shown in FIG. 8. The ammonia and urea production (metabolism) rates of strain JHH-7 were measured by the same method in the comparative example and results are shown in FIG. 9.

What is claimed is:

1. Human hepatoma-derived cell line FLC-4, FERM BP-5165.

2. A method for producing a useful polymer by culturing the cell line of claim 1 in a culture medium under conditions effective to produce said useful polymer with a radial-flow type bioreactor and recovering said useful polymer.

3. A method for producing albumin by culturing the cell line of claim 1 in a culture medium under conditions effective to produce said albumin with a radial-flow type bioreactor and recovering said albumin.

4. A method for producing a useful polymer by culturing the cell line of claim 1 in a culture medium under conditions effective to produce said useful polymer and recovering said useful polymer.

5. The method as claimed in claim 4, wherein the useful polymer is albumin.

* * * * *